United States Patent [19]
Coulter et al.

[11] Patent Number: 5,657,764
[45] Date of Patent: Aug. 19, 1997

[54] DEVICE AND METHOD FOR DETERMINING THE LENGTH OF A URETHRA

[75] Inventors: Christopher C. Coulter, Newton Upper Falls; Carl J. Wisnosky, Spencer, both of Mass.; Leo C. Felice, Pascoage, R.I.; Thomas Ventres, Millbury, Mass.; Victor E. Grigoriev, Las Vegas, Nev.

[73] Assignee: UroMed Corporation, Needham, Mass.

[21] Appl. No.: 521,246

[22] Filed: Aug. 30, 1995

[51] Int. Cl.⁶ .................................................. A61B 5/103
[52] U.S. Cl. ................................... 128/778; 606/1
[58] Field of Search ...................... 128/774, 775, 128/778; 600/29, 30, 31; 604/102, 203; 606/102

[56] References Cited

U.S. PATENT DOCUMENTS

| | | |
|---|---|---|
| 3,706,307 | 12/1972 | Hasson . |
| 3,797,478 | 3/1974 | Walsh et al. ............................ 600/29 |
| 3,854,469 | 12/1974 | Giori et al. ............................ 600/31 |
| 3,941,131 | 3/1976 | Ogle ................................... 604/203 |
| 3,977,408 | 8/1976 | MacKew ............................... 604/102 |
| 4,016,867 | 4/1977 | King et al. . |
| 4,121,572 | 10/1978 | Krzeminski . |
| 4,489,732 | 12/1984 | Hasson . |
| 4,500,313 | 2/1985 | Young . |
| 5,002,558 | 3/1991 | Klein et al. . |
| 5,010,892 | 4/1991 | Colvin et al. ......................... 128/774 |
| 5,013,318 | 5/1991 | Spranza, III . |
| 5,034,009 | 7/1991 | Mouchel ............................... 606/1 |
| 5,131,906 | 7/1992 | Chen .................................. 600/29 |
| 5,186,180 | 2/1993 | Bellas ................................ 128/778 |
| 5,306,226 | 4/1994 | Salama . |
| 5,352,182 | 10/1994 | Kalb et al. ........................... 600/30 |

FOREIGN PATENT DOCUMENTS

WO90/04431  5/1990  WIPO .

*Primary Examiner*—Michael Buiz
*Assistant Examiner*—Patrick Rasche
*Attorney, Agent, or Firm*—Lorusso & Loud

[57] ABSTRACT

There is presented a urethral measuring device for determining the length of a human urethra, the measuring device comprising a member having an expandable portion at a first end and adapted to receive fluid from an external source at a second end. The member includes graduations arranged such that the graduations are located a pre-specified distance from the expandable portion. In certain embodiments, the graduations also are located at least "x" distance from the meatus of the urethra when the device is inserted and in an operative position. The measuring device further includes a collar slidably disposed and movable on the member and is used as a pointer against the graduations to measure the length of the urethra. There is further presented a method for determining the length of a urethra, utilizing the aforesaid device.

13 Claims, 7 Drawing Sheets

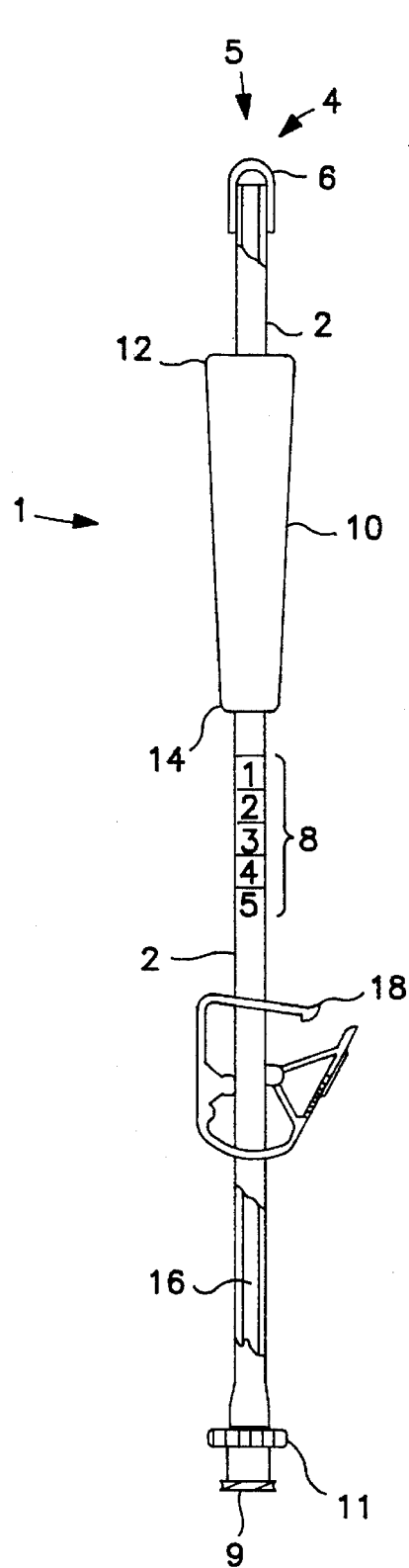
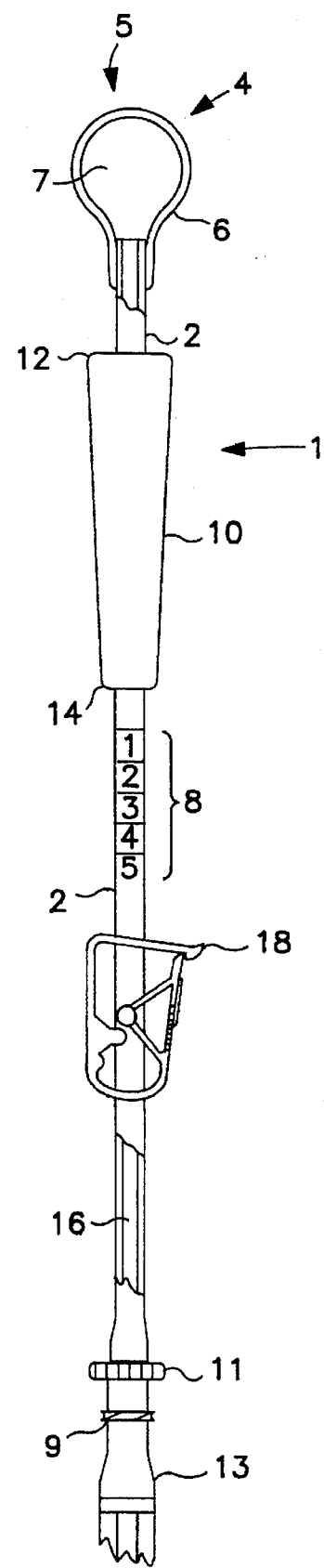
FIG. IA
FIG. IB

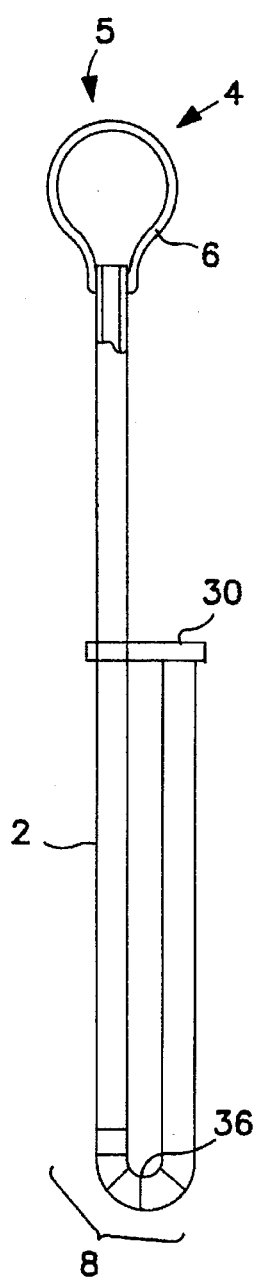
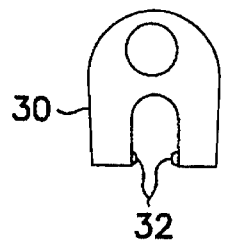
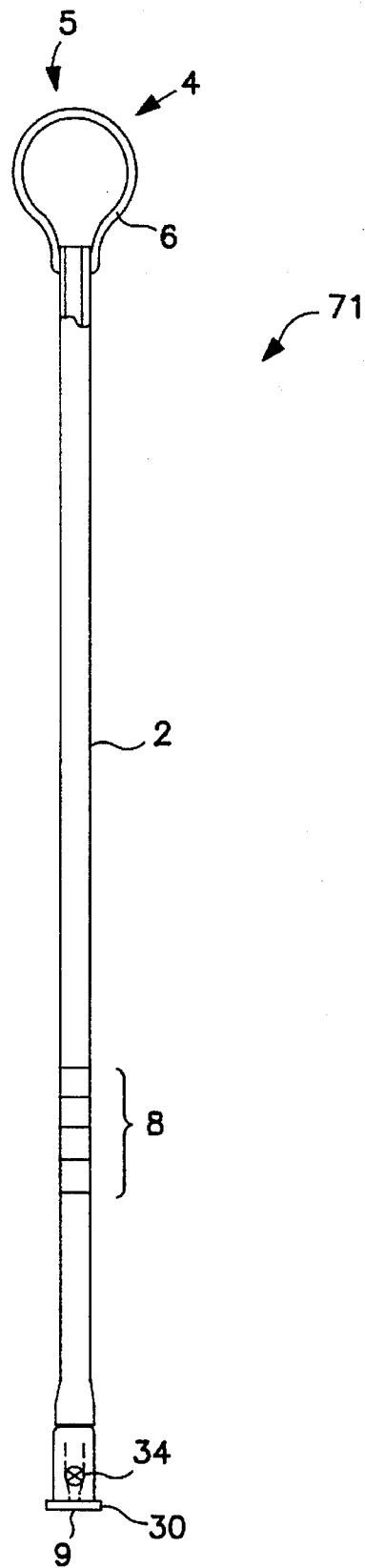
FIG. 7C
FIG. 7B
FIG. 7A

DEVICE AND METHOD FOR DETERMINING THE LENGTH OF A URETHRA

BACKGROUND OF THE INVENTION

(1) Field of the Invention

This invention relates generally to measuring devices for use in medical applications and is directed more particularly to a device and method for measuring the length of a human urethra.

(2) Description of the Prior Art

Urinary incontinence is a widespread medical affliction suffered by approximately 11 million adults in the United States. There are in existence a variety of urethral occlusion devices to aid in the control of urinary incontinence. However, in order for certain occlusion devices to be comfortable and effective in minimizing leakage around the device, they must be accurately sized according to the length of the intended patient's urethra.

Several sizing devices for measuring body cavities are known in the art. In U.S. Pat. No. 5,352,182, there is disclosed a void-through urethral catheter and an accompanying sizing device to determine the proper size for the disclosed catheter. In use, the sizing device is first reconfigured so that it is sufficiently narrow in diameter for insertion into the urethra. Accordingly, a rod must be inserted into a shaft of the device until the rod contacts the mushroom-shaped distal end of the shaft. The rod is then advanced further, longitudinally extending the end of the shaft to reduce the diameter thereof. Using the rod, the shaft is inserted into the urethra and advanced until the device reaches the bladder. The rod is then removed, allowing the mushroom-shaped end of the shaft to drop against the bladder neck. A removable disk on the shaft's opposite end is moved along the shaft until it contacts the urethral meatus. Markings on the shaft indicate a range of catheter sizes, and the marking on the shaft where the disk abuts the meatus represents the particular size needed for proper fit.

The above-described device is deficient in that it requires the operator to read the marking on the shaft immediately adjacent to the external urethral meatus. It is difficult to obtain an accurate reading at this location due to the marking being obscured by the labial tissues. Also, since the disk is a thin, cylindrical object, it is difficult to manipulate with the fingers and properly position the disk due to the spongy nature of the urethral tissues, and further due to the positioning of the disk between the labia and the meatus.

Moreover, this sizing device is disadvantageous in that it requires the preliminary step of reconfiguring the shape of the device prior to insertion into the urethra. Further, it would appear that the disk must be slid onto the shaft after the shaft has been inserted into the urethra and secured in the bladder neck. This increases the steps required to configure the device for measuring and further illustrates the cumbersome nature of the device.

U.S. Pat. No. 4,500,313 discloses a urethral catheter that determines the length from the meatus to the sphincter. This catheter has an inner member open at an end adapted to be inserted into the urethra, and an outer sleeve into which the inner member is received. The inner member includes calibrated markings that are spaced from the open end of the inner member by a distance equal to the length of the outer sleeve.

To determine the length, the operator holds a flared end of the outer sleeve in a fixed position against the external meatus while feeding the inner member therethrough into the urethra. The inner member is advanced until urine enters its open end and flows through the inner member, indicating that the catheter is past the sphincter. The inner member is then withdrawn until the flow of urine stops, indicating that the device is below the sphincter. The length from the meatus to the sphincter is then determined by reading the calibrated marking on the inner member at the location of the non-flared end of the outer sleeve.

While the above device may be beneficial in that it allows for measurements to be taken at a distance from the meatus, the length from the meatus to the sphincter is not always an accurate representation of the length of the urethra because the location of the sphincter muscle varies from individual to individual. Thus, the device is of questionable use in determining an appropriately sized urethral occlusion device. The device is also cumbersome to use as it requires manipulations of the inner member until the sphincter is located. Once located, there is no means for anchoring the inner member in the bladder neck to prevent slippage therefrom while a reading is taken. Additionally, since the flow of urine and its subsequent stoppage is the indicator that the device is properly located for measuring, the device requires that there be sufficient urine present in the bladder to perform the measurement. Further, since urine is flowing into and through the inner member, the connection of a bag to the inner member is required to collect the urine. This increases the possibility that the operator may soil his hands with urine from the patient, resulting in an unsanitary procedure as well as requiring disposal of the collected urine.

There is thus a need for a urethral measuring device that eliminates the deficiencies in the prior art. The device must be simple in construction and easy to use, and must be capable of providing measurements irrespective of the volume of urine in the patient's bladder. The device must also be capable of providing accurate measurements of the length of the urethra which are easily observable while the device is positioned within the urethra.

SUMMARY OF THE INVENTION

An object of the invention is, therefore, to provide a device capable of accurately and easily determining the length of a human urethra.

A further object of the invention is to provide a device for determining the length of a urethra wherein the measurements of length are observed at a distance from the meatus of the urethra.

Another object of the invention is to provide a device for determining the length of a urethra which minimizes risk of infection when obtaining the measurements of length of the urethra.

Another object of the invention is to provide a device for determining the length of a urethra which is simple in design, easy and comfortable to use, and inexpensive to manufacture.

A still further object of the invention is to provide a method for determining the length of a human urethra, utilizing the aforesaid device.

With the above and other objects in view, as will hereinafter appear, a feature of the present invention is the provision of a device for determining the length of a urethra having a hollow member with an expandable portion at a first end thereof and being open at its opposite end. The hollow member is of a length greater than the length of the urethra to be measured. The hollow member includes measuring graduations on its surface, which are located a pre-specified distance from the expandable portion. Additionally, the graduations are located at least "x" distance from the meatus of the urethra when the hollow member is inserted into the urethra, expanded in the bladder, and anchored in the bladder neck. Preferably, "X" is a distance of at least one inch or greater.

The measuring device of the invention also includes a non-removable collar permanently affixed to the hollow member, and having a pre-specified length. The collar is slidably disposed on the hollow member and freely movable thereon. The collar has a first end which, when the measuring device is anchored in the bladder neck, is caused to contact the meatus of the urethra. The second end of the collar is used as a pointer against the graduations on the hollow member. The graduations observed at the second end of the collar represents the length of the urethra. The graduations are easily read by the operator since the graduations are located at least "x" distance from the meatus, with "x" distance being sufficient to assure that the graduations are not obscured by the tissues surrounding the meatus.

The open end of the hollow member is in fluid communication with the expandable portion of the hollow member, and is adapted to receive fluid from a source external to the device. The expansion of the expandable portion is achieved via transmission of fluid from the external fluid source to the expandable portion. A clamp or similar valving device is provided on the hollow member for selectively occluding the hollow member, thereby controlling the expansion of the expandable portion, and the reversal thereof.

In a further embodiment, the device of the instant invention includes a collar having graduations provided thereon, and a reference marking provided on the hollow member. The collar may include a longitudinal slot or a transparent material that allows the reference marking to be observed along with the graduations, to determine the length of the urethra. The reference marking may comprise a single mark or a shaded portion on the hollow member. For this embodiment, the "x" distance from the meatus is at least ½ inch or greater.

In yet another embodiment of the invention, the device comprises a hollow member having graduations thereon at a fixed distance from the first end of the hollow member. The hollow member includes a thermochromic material or coating capable of changing color in response to the heightened temperature of the body. The length of the urethra is determined by observing the graduation located at the point of color change on the hollow member.

In yet another embodiment of the invention, the device comprises a hollow member, a portion of which includes a plurality of beads spaced equally apart from one another. Each bead is located a pre-specified distance from the first end of the hollow member and is representative of the length of a urethra. To determine the length of the urethra, at least one of the beads is observed at the meatus when the hollow member is inserted into the urethra and the expandable portion is anchored in the bladder neck. Each bead may further include a graduation indicative of the prespecified distance from the first end of the hollow member.

In a further embodiment, the hollow member is designed to fold back upon itself so the length of the urethra can be determined by reference to graduations located a pre-specified distance from the first end of the hollow member. The device includes means to secure the hollow member in its folded condition. The length of the urethra can be determined while the device is in operation, or after removal of the device.

Alternatively, the hollow member can be inserted into the urethra, inflated, and anchored in the bladder neck. A reference mark is placed on the hollow member at the location where the hollow member meets the meatus. The length of the urethra is determined after the hollow member is removed from the urethra by measuring the distance from the reference mark to the first end of the hollow member.

In accordance with a further feature of the invention, there are disclosed methods of determining the length of a urethra by using any of the aforesaid devices.

The above and other features of the invention, including various novel details of construction and combination of parts, will now be more particularly described with reference to the accompanying drawings and pointed out in the claims.

BRIEF DESCRIPTION OF THE DRAWINGS

Reference is made to the accompanying drawings in which are shown illustrative embodiments of the invention from which its novel features and advantages will be apparent.

In the drawings:

FIG. 1A shows a first embodiment of the urethral measuring device of the invention, in a non-expanded condition.

FIG. 1B shows the first embodiment of the urethral measuring device of the invention, in an expanded condition.

FIGS. 7A–C show a seventh embodiment of a fold-back urethral measuring device of the invention, in an expanded condition.

DESCRIPTION OF THE PREFERRED EMBODIMENTS

Figure 2:
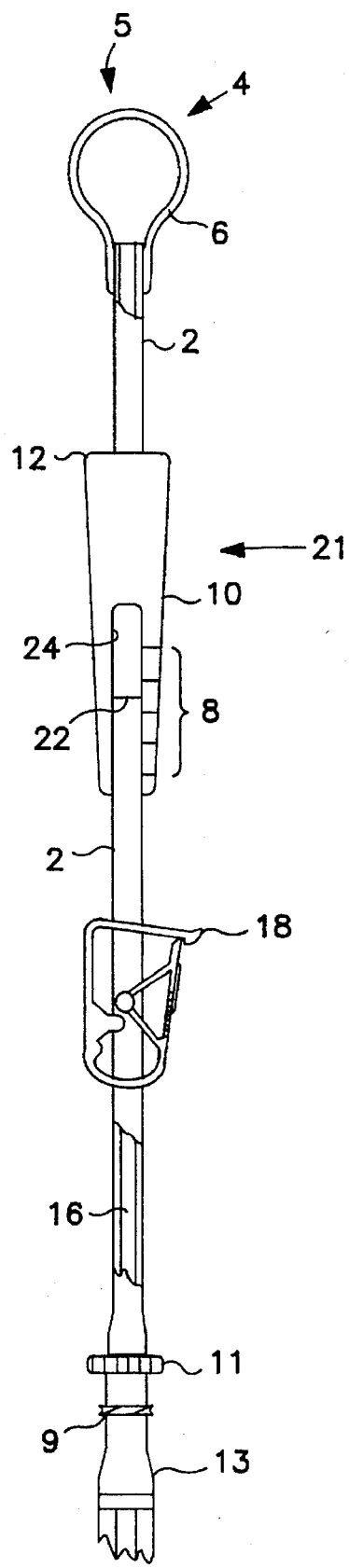
FIG. 2 shows a second embodiment of the urethral measuring device of the invention, in an expanded condition.

Referring to FIGS. 1A and 1B, it will be seen that an illustrative embodiment of the measuring device 1 of the invention includes a hollow member 2 substantially cylindrical in shape and having a length greater than the length of a normal human urethra. The hollow member 2 has an expandable portion 4 at a first end 5 of the hollow member 2. The hollow member 2 is comprised of a biocompatible material having characteristics of flexibility. The biocompatible material and the construction of the hollow member allows it to conform to the natural shape of the urethra, thereby preventing deformation thereof. Suitable materials for the biocompatible material include, but are not limited to, thermoplastic elastomers and materials similar thereto, in particular, polyurethanes (or other similar thermoplastic urethanes), poly-vinyl chloride, silicone, latex or other rubbers.

The expandable portion 4 may comprise a flexible membrane, or balloon 6, which is attached to the distal end of the hollow member 2 by thermal bonding, laminating or other means. Suitable biocompatible materials for the balloon 6 have been found to be the aforementioned thermoplastic elastomers, thermoplastic urethanes, poly-vinyl chloride, silicone, latex or similar rubbers.

In its pre-insertion configuration, the balloon 6 is adapted to rest against the hollow member 2. The balloon 6 possesses a contracted shape with a rounded tip for easy insertion and removal of the hollow member 2 through the opening of the urethra (FIG. 1A), and a larger, expanded shape for anchoring the hollow member in the bladder neck (FIG. 1B). By anchoring the balloon 6 in the bladder neck so as to secure the hollow member 2 therein, movement of the device 1 will be arrested, thereby allowing accurate measurements of the length of the subject urethra to be obtained.

To achieve such anchoring, the interior 7 of balloon 6 is in fluid communication with an open second end 9 of the hollow member 2. A fitting 11 or similar device known in the art is connected to the open second end 9 of the hollow member 2 for interconnecting an external fluid source 13 to the hollow member 2. A fluid, such as air or liquid, is introduced into the open second end 9 by coupling the external fluid source 13, such as the nozzle of a syringe or an inflator, to the fitting 11. The fluid is thus able to pass into a passage 16 defined by hollow member 2, and into the interior 7 of the balloon 6.

The expansion and contraction of the balloon 6 is selectively controlled by means of a clamp 18, disposed on the hollow member 2 above the fitting 11. The clamp 18 acts on, and locally distorts the shape of, the hollow member 2 to selectively occlude the hollow member 2. When it is desired to admit or expel fluid, the clamp 18 is positioned in its open state, as shown in FIG. 1A. FIG. 1B shows the clamp 18 in its closed state occluding the hollow member 2, thereby maintaining the balloon in its expanded state and preventing the fluid from escaping.

Figure 3A:
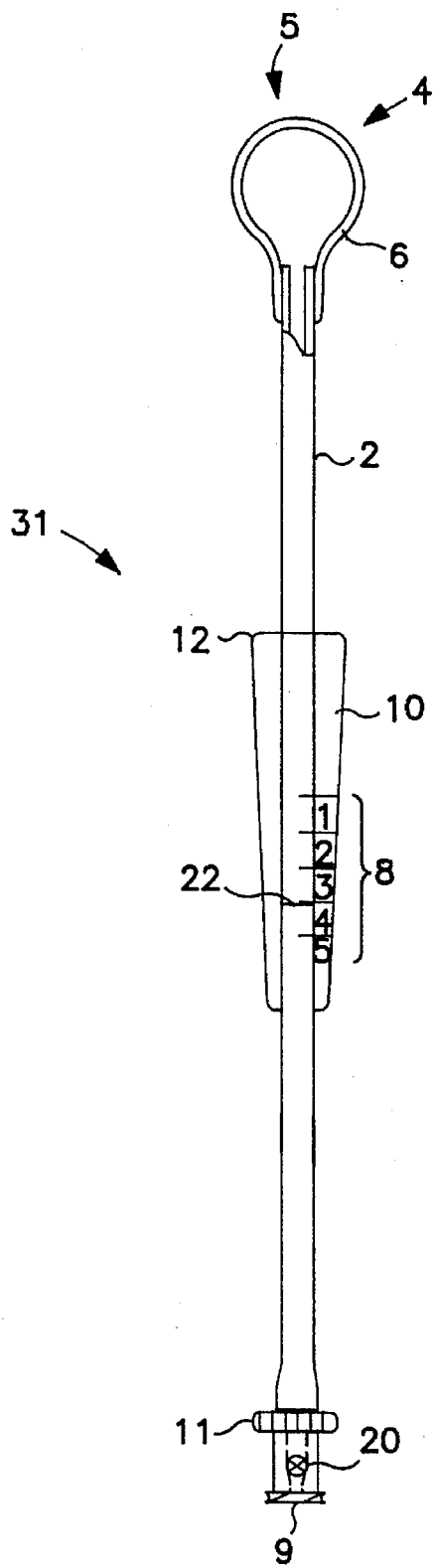
FIG. 3A shows a third embodiment of the urethral measuring device of the invention, in an expanded condition.
Figure 3B:
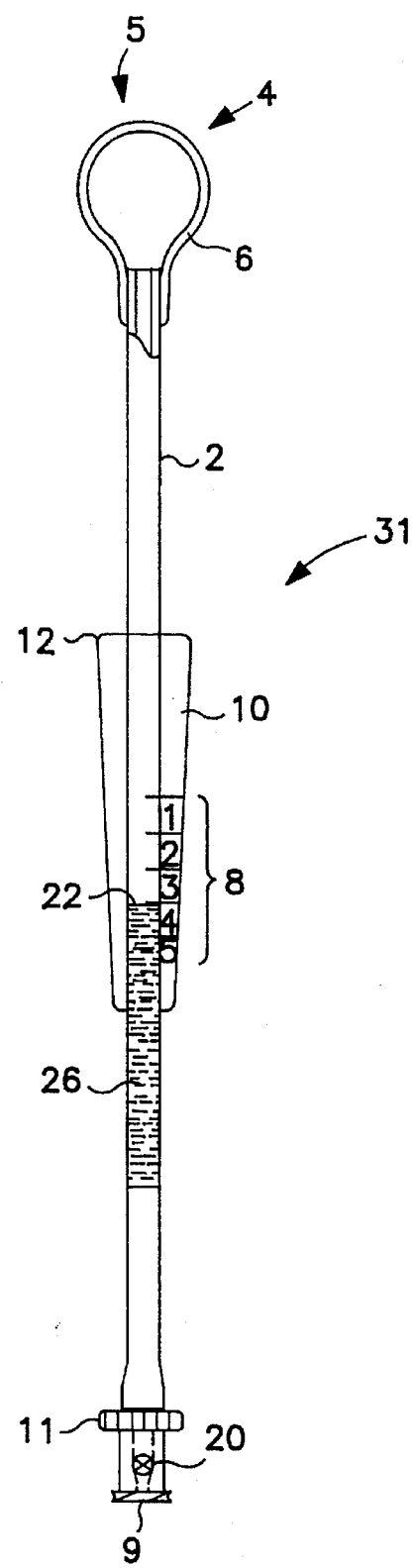
FIG. 3B shows the third embodiment of the urethral measuring device of the invention, with an alternative point of reference for obtaining the measurement of the urethra.

The measuring device 1 in FIGS. 1A and 1B alternatively may be configured with a releasable check valve, such as valve fitting 20 shown in FIGS. 3A and 3B, to control the expansion and contraction of the balloon 6. As a further alternative, the fluid may be introduced into the device 1 at the open second end 9 of the hollow member 2 by means of connecting the external fluid source 13 to the open second end 9. Upon sufficient expansion of the expandable portion 4, the expansion is maintained by leaving the external fluid source 13 connected to the open second end 9 of the hollow member 2. Upon completion of the measuring process, the external fluid source 13 is simply removed, causing the expandable portion 4 to deflate.

The hollow member 2 further includes graduations 8 arranged thereon, which are located a pre-specified distance from the first end 5 of the hollow member 2. The graduations 8 on the hollow member 2 are so calibrated as to be representative of the length of a urethra. The location of the graduations 8 on the hollow member 2 is at least "x" distance from the meatus of the urethra when the hollow member 2 is inserted into the urethra and anchored in the bladder neck, with "x" being preferably at least 1 inch or greater. This feature is advantageous in that it enables the operator to obtain an accurate reading of the urethra's length from the graduations 8 on the hollow member, which are distanced from the meatus. Without this feature, the reading would be taken from calibration marks located immediately adjacent to the meatus, which may be obscured by the labial tissues and therefore, difficult to read.

The device 1 further includes a non-removable collar 10 that is slidably disposed and movable on said hollow member 2. The collar 10, in conjunction with the graduations 8 on the hollow member 2, is used to measure the length of the urethra. The collar 10 has a first end 12 and a second end 14 and is disposed between the hollow member first end 5 and the hollow member second end 9. The collar first end 12 is adapted to contact and rest against the meatus of the urethra when the device is in use. The collar 10 may be configured in a number of geometrical shapes, and preferably is configured in a truncated conical shape with the wide end at the collar first end 12. In general, the shape of the collar first end 12 is designed so as to minimize or avoid discomfort and damage to the surrounding tissues when the first end 12 is in contact with the meatus. Additionally, to improve measurement accuracy, the collar first end 12 may be configured to correspond with the shape of the meatal plate of the intended urethral occlusion device.

The collar 10 has a pre-specified length of at least 1 inch or greater which, when the device is inserted and anchored in the bladder neck, is a sufficient distance from the meatus and surrounding labial tissues to allow for easy reading of the graduations at said collar second end 14. The length of the collar 10, as well as its overall shape, is also designed so as to provide a sufficiently sized gripping surface for the operator to slide the collar 10 along the hollow member 2, preferably without the operator contacting the meatus and/or labia during insertion of the device or when taking a measurement. Since the measuring device 1 should be in a sterile condition before use, minimizing contact with the meatus and surrounding tissues should reduce the risk of infection.

In use, the operator attaches the nozzle of a syringe, or other external fluid source 13, to the fitting 11, thereby placing the external fluid source 13 in fluid communication with the open second end 9 of the hollow member 2. The rounded or atraumatic tip of the hollow member 2 is inserted into the urethra until the expandable portion 4 is positioned in the bladder. The operator actuates the external fluid source 13 (e.g. depresses the plunger of a syringe), causing fluid to pass from the external fluid source 13 into the open second end 9 of the hollow member and, ultimately, into the interior 7 of the balloon 6. Upon sufficient inflation of the balloon 6 (e.g. 4 ml), the hollow member 2 is retracted slightly by the operator to rest the balloon 6 against the bladder neck. This forms a seal with the walls of the bladder neck and securely anchors the first end 5 of the hollow member 2 therein.

At such time when sufficient fluid has been introduced to anchor the balloon 6 in the bladder neck, the operator occludes the passage 16 of the hollow member 2 by actuating the clamp 18, thus preventing further flow of fluid into or out of the device 1. The operator disconnects the external fluid source 13 from the open second end 9 of the hollow member 2. The operator slides the collar 10 along the hollow member 2 until the collar first end 12 abuts the meatus of the subject urethra. The operator now observes the position of the collar second end 14 and notes the graduation 8 at that position on the hollow member 2. The graduation 8 is easy to read as it is located at least "x" distance from the meatus of the urethra, with the preferred distance of "x" being at least 1 inch or greater. Because of the predetermined length of the collar 10 and the calibrated location of the graduations 8 on the hollow member 2, the specific graduation noted at the collar second end 14 is representative of the length of the urethra.

When the measurement process is completed, the operator opens the clamp 18 and thereby opens the passage 16 in the hollow member 2. The hollow member 2 is allowed to return to its undistorted state. The fluid in the balloon 6 is expelled, causing the balloon 6 to deflate. The device 1 is removed from the urethra by simply pulling on the external proximal end of the hollow member 2.

Referring to FIG. 2, there is shown an alternative embodiment of a device 21 in which the collar 10 is configured with a longitudinal slot to form a window 24 therein. In this embodiment, the graduations 8 are located on the collar 10, as shown in the figure. The hollow member 2 includes a reference marking 22 located a pre-specified distance from the first end 5 of the hollow member 2. The reference marking 22, in conjunction with the graduations 8, provides a means for measuring the length of the urethra. While the window 24 is illustrated as a slot terminating at one end of the collar 10, this is not a limitation as the slot-like aperture requires only that its length extend along the graduations 8 on the collar 10. All other aspects of the device 21 are similar to the measuring device 1 described with reference to FIGS. 1A and 1B.

Using the measuring device of FIG. 2, the operator inserts the hollow member 2 into the urethra until the expandable portion 4 is positioned in the bladder. In the manner described in the aforementioned method, the operator inflates the expandable portion 4 in the bladder and positions the expandable portion 4 against the bladder neck, forming a seal with the walls of the bladder neck and securely anchoring the first end 5 of the hollow member 2 therein. The operator occludes the passage 16 of the hollow member 2 by actuating the clamp 18 or valve fitting 20 (FIGS. 3A,B). Alternatively, the expansion is maintained by keeping the external fluid source 13 connected to the open second end 9.

The operator slides the collar 10 along the hollow member 2 until the collar first end 12 abuts the meatus of the subject urethra. Looking at the window 24 in the collar 10, the operator locates the reference marking 22 and observes the graduation 8 on the collar 10 proximate the reference marking 22. The specific graduation noted is representative of the length of the urethra. Similar to the aforementioned embodiment, the graduations 8 are easily read since they are located at least "x" distance from the meatus of the urethra, with "x" being at least ½ inch or more in this embodiment.

In FIGS. 3A and 3B, it will be seen that still another illustrative embodiment of the invention includes a collar 10 comprised of a transparent plastic material having the graduations 8 on the transparent collar 10. Suitable materials for the transparent plastic material include, but are not limited to, acrylic, polycarbonate, polypropylene, and polystyrene materials. As in FIG. 2, there is provided a reference marking 22 on the hollow member 2 (FIG. 3A) which, in conjunction with the graduations 8, is used to provide a measurement of the length of a urethra. Alternatively, the reference marking 22 may comprise shading 26 on the hollow member 2, as shown in FIG. 3B, for additional ease in locating the reference marking 22.

As noted above, the device 31 illustrated in FIGS. 3A and 3B includes a valve fitting 20, such as a pinch or check valve. The valve fitting 20, similar to the clamp 18 of FIGS. 1A, 1B and 2, selectively occludes the flow of fluid through the hollow member 2 so the expandable portion 4 can be expanded or contracted. While the valve fitting 20 is illustrated, the device 31 of FIGS. 3A and 3B may be configured with the clamp 18 and fitting 11 of FIGS. 1A, 1B and 2. Alternatively, the flow of fluid into and out of the device 31 can be controlled by maintaining the interconnection between the external fluid source 13 and the open second end 9 of the hollow member 2.

When it is desired to measure the length of a urethra, the operator inserts the device 31, inflates the expandable portion 4 in the bladder, and anchors the first end 5 in the bladder neck, as hereinabove described. The operator slides the collar 10 along the hollow member 2 until the collar first end 12 abuts the meatus of the urethra. Looking through the transparent collar 10, the operator locates the reference marking 22 on the hollow member 2 and observes the graduation 8 on the collar 10 proximate the reference marking 22. The specific graduation noted is representative of the length of the urethra. The cooperating graduation 8 is easily read since it is located at least "x" distance from the meatus of the urethra, with "x" being at least ½ inch or more. After obtaining the measurement, the operator actuates the valve fitting 20, or clamp 18, thereby contracting the expandable portion and removing the hollow member 2 from the urethra. Alternatively, contraction of the expandable portion 4 may be accomplished by removing the external fluid source 13 from the open second end 9 of the hollow member 2.

Figure 4:
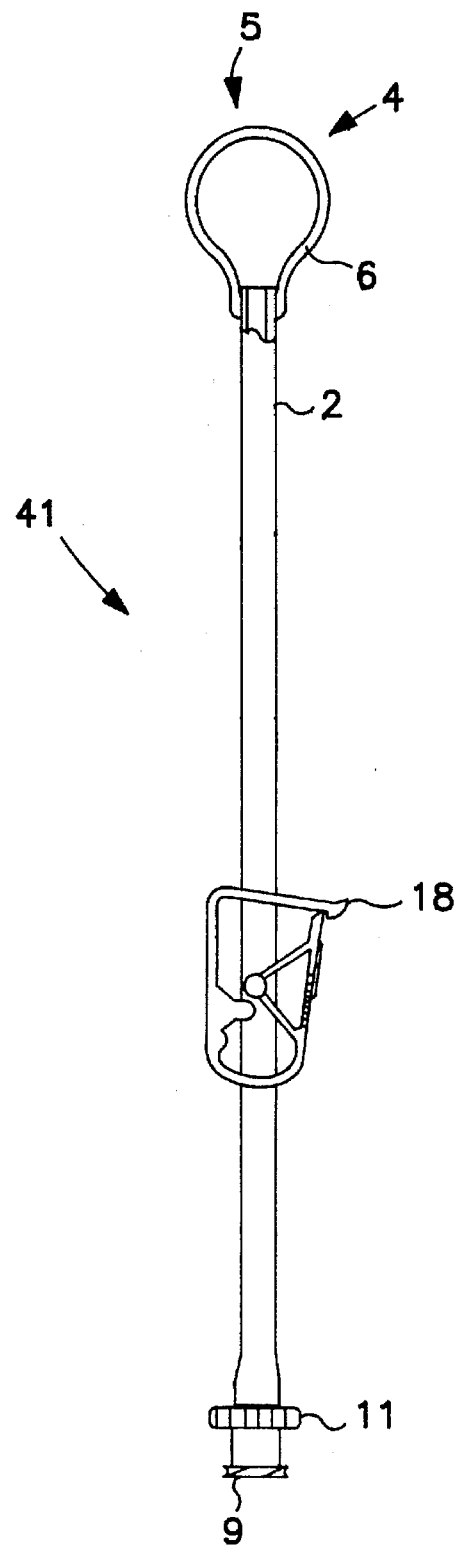
FIG. 4 shows a fourth embodiment of the urethral measuring device of the invention, in an expanded condition.

In FIG. 4, there is shown an alternative embodiment of the invention in which the measurement of the length of the urethra is determined without the use of a collar disposed on the device 41. In addition, the hollow member 2 is free of graduations 8 on the hollow member 2. All other aspects of the device 41 are similar to the measuring devices described in FIGS. 1A and 1B. While the fitting 11 and clamp 18 are illustrated as means for introducing the fluid into the device 41 and controlling the expansion of the expandable portion 4, the device of FIG. 4 may be configured with the valve fitting 20, as shown in FIGS. 3A and 3B, to accomplish these functions. Alternatively, the fluid may be introduced into the device 41, and its expansion controlled, by maintaining the interconnection between the external fluid source 13 and the open second end 9 of the hollow member 2.

In use, the operator inserts the hollow member 2 into the urethra until the expandable portion 4 is positioned in the bladder. In the manner described in the aforementioned methods, the operator inflates the expandable portion 4 in the bladder and retracts the hollow member 2 until the expandable portion 4 is snugly positioned against the bladder neck. A seal is thus formed with the walls of the bladder neck, thereby securely anchoring the first end 5 of the hollow member 2 therein. The expansion of the device 41 is maintained while the urethra is measured, with the expansion being maintained by any of the means discussed with reference to the aforementioned embodiments. With the device 41 inserted and optimally snug in the bladder neck, the operator observes the point on the hollow member 2 where the hollow member 2 enters the meatus, and marks this site with any suitable marker, such as a surgical marker.

The device 41 is then deflated and removed, and a measurement is taken of the length of the device from the first end of the hollow member 2 to the marking on the hollow member. The measurement obtained is representative of the length of the urethra. The measurement may be obtained using a measuring means such as a ruler or template having graduations representative of length.

Figure 5:
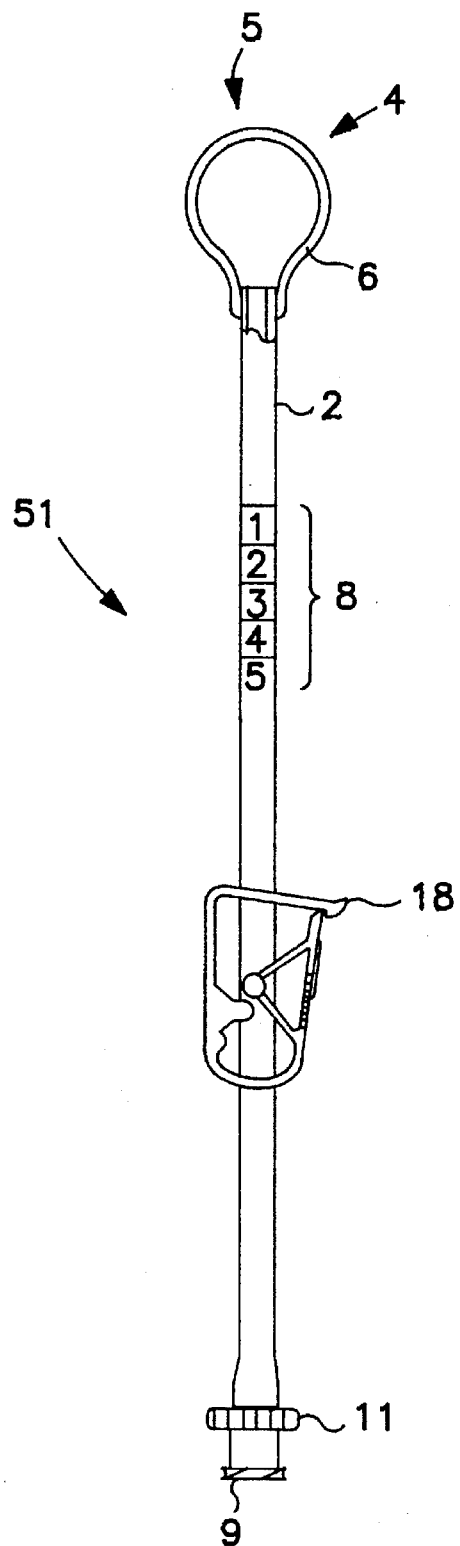
FIG. 5 shows a fifth embodiment of the urethral measuring device of the invention, in an expanded condition, utilizing a thermochromic material.

In FIG. 5, there is shown an alternative embodiment of the device 41 of FIG. 4 in which the hollow member 2 is comprised of a thermochromic material capable of changing color in response to body temperature. The thermochromic material may comprise an ink, a coating, or other materials known in the art that provide a visual indication responsive to a specific temperature. The thermochromic material may be applied either to the inner or outer surface of the hollow member 2. Alternatively, the thermochromic material may be integrated with the biocompatible material of the hollow member during the molding or manufacturing process.

The hollow member in this embodiment includes graduations 8 located a pre-specified distance from the first end 5 of the hollow member 2, and each graduation is representative of a length of a urethra. The hollow member 2 may be comprised in whole or in part of the thermochromic material, but at least the portion of the hollow member 2 surrounding the graduations 8 must be comprised of the thermochromic material. Alternatively, the graduations 8 may be comprised of the thermochromic material. All other aspects of the device 51 are similar to the measuring device described in FIG. 4.

To measure the length of a urethra using this device, the operator inserts, inflates and positions the device 51 according to any one of the methods disclosed in the above embodiments. Once the expandable portion 4 of the hollow member 2 is snugly seated in the bladder neck, the operator allows the device 51 to remain in the body for a period of time, preferably 2–5 minutes, to expose the thermochromic material to the heightened temperature inside the body. At the expiration of such time, or a time deemed by the operator to be sufficient, the operator reverses the expansion of the device 51, according to any one of the aforementioned methods, and removes the device 51 from the urethra. The operator then observes the hollow member 2 to determine where the color has changed on the hollow member 2. The specific graduation 8 at the point of color change indicates the length of the urethra.

Figure 6:
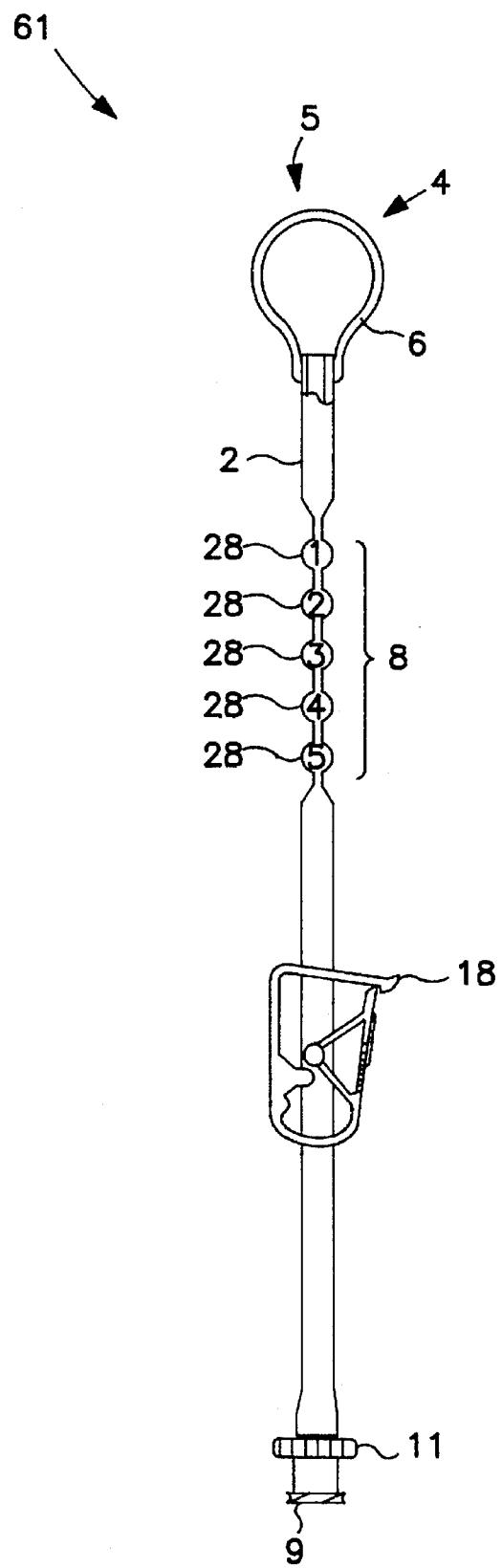
FIG. 6 shows a sixth embodiment of the urethral measuring device of the invention, in an expanded condition, having a plurality of beads.

FIG. 6 illustrates another embodiment of the invention in which a portion of the hollow member 2 is formed to provide a plurality of bead-like structures spaced equally apart from one another in a pre-defined pattern. Each of the plurality of beads 28 on the hollow member 2 is located a fixed distance from the first end 5 of the hollow member 2, and each bead is marked with a graduation 8 representative of a specific length of a urethra. All other aspects of the device 61 are similar to the measuring devices described in the aforementioned embodiments, and any of the disclosed means for introducing fluid into the device and controlling its expansion, may be used interchangeably in this embodiment.

In use, the operator inserts the hollow member 2 into the urethra until the expandable portion 4 is positioned in the bladder. In the manner described in the aforementioned methods, the operator inflates the expandable portion 4 in the bladder and retracts the hollow member 2 until the expandable portion 4 is snugly positioned against the bladder neck. A seal is thus formed with the walls of the bladder neck, thereby securely anchoring the first end 5 of the hollow member 2 therein. The expansion of the device 61 is maintained while the urethra is measured, with the expansion being maintained by any of the means discussed with reference to the aforementioned embodiments.

With the device 61 inserted and optimally snug in the bladder neck, the operator observes the particular bead 28 abutting the meatus, including the graduation 8 thereon. The operator determines the length of the urethra by directly observing the particular bead abutting the meatus. Alternatively, the operator marks the site on the bead 28 with any suitable marker and determines the length of the urethra by observing the marked bead. After determining the length, the expansion of the device 61 is reversed and removed in the fashion described in any of the aforementioned embodiments. However, if it is difficult to read or observe the marked bead, due to the obscuring of the bead by the meatal and/or labial tissues, then the marked bead may be read upon removal from the urethra.

FIGS. 7A–C show yet another embodiment of the invention further including a snap-on, U-shaped fitting 30 attached to the hollow member 2 at the open second end 9 thereof. The U-shaped fitting 30 comprises projections 32 (FIG. 7B) to secure the U-shaped fitting 30 to the hollow member 2 when the device 71 is in operation. The hollow member 2 in this embodiment includes graduations 8 located a pre-specified distance from the first end 5 of the hollow member 2, where each graduation is representative of a length of a urethra. A check valve 34 that is integral with the U-shaped fitting 30 is the preferred means for introducing the fluid into the device 71, and controlling the expansion of the expandable portion 4.

As in the aforementioned embodiments, the device 71 is inserted into the urethra, inflated in the bladder, and retracted into the bladder neck where it rests against the bladder neck to anchor therein. In this position, the operator takes hold of the proximal portion of the hollow member 2, which extends from the urethra, and bends the proximal portion back upon itself until the U-shaped fitting 30 contacts the meatus. The U-shaped fitting 30 is then secured to the hollow member 2 by means of the projections 32 forming a snap-fit with the hollow member 2.

The operator observes the graduations 8 located at the fold of the hollow member 2 and particularly notes the graduation 8 located at the midpoint 36 of the fold (FIG. 7C), which graduation is representative of the length of the urethra. The graduations 8 are located a sufficient distance from the meatus and surrounding tissues to allow for easy reading by the operator. Alternatively, the midpoint 36 of the fold can be marked with a suitable marker, and the marking read following removal of the device 71. Removal is accomplished by pinching or squeezing the check valve, which opens the valve and allows the fluid to drain from the device 71.

While the invention has been particularly shown and described with reference to the aforementioned embodiments, it will be understood by those skilled in the art that various changes in form and detail may be made therein without departing from the spirit and scope of the invention. Thus, any modification of the shape, configuration and composition of the elements comprising the invention is within the scope of the present invention. For example, the means for fluidly expanding the expandable portion 4 described above may be substituted with means for mechanically expanding an expandable member. Such mechanical means for expanding an expandable member, such as a balloon, is fully disclosed in U.S. Ser. No. 08/062,592, filed May 17, 1993 U.S. Pat. No. 5,483,476, issued on Jan. 16, 1996. Additional means for expanding an expandable member is found in U.S. Ser. No. 08/267,487, filed Jun. 29, 1994, in which there is disclosed a foam or elastomer body positioned and moveable within a member having an expandable end, whereby the member is acted upon such that the foam or elastomer body is moved through the member into its expandable end to expand the end in balloon-like fashion. Either mechanism will function to anchor the urethral measuring device of the invention in the bladder neck so that accurate measurements can be taken.

Having thus described the invention, what we claim as new and desire to secure by Letters Patent of the United States is:

1. A device for determining the length of a urethra comprising:

a hollow member having an expandable portion at a first end and a length greater than the length of the urethra to be measured;

wherein said hollow member further includes a plurality of beads spaced equally apart from one another in a pre-defined pattern, each of the plurality of beads being located a prespecified distance from the first end of the hollow member, and being representative of a length of the urethra;

wherein at least one of said plurality of beads is observable at the meatus when said hollow member is inserted into the urethra and said expandable portion anchors in the bladder neck.

2. The device of claim 1 wherein said hollow member further comprises an open second end in fluid communication with said expandable portion.

3. The device of claim 2 wherein said expandable portion comprises a flexible membrane affixed to said hollow member, said flexible membrane being in fluid communication with said open second end.

4. The device of claim 2 wherein said open second end of said hollow member is adapted to receive fluid from an external source, whereby expansion of said expandable portion occurs upon transmission of fluid from said external fluid source to said expandable portion.

5. The device of claim 1, further comprising means for maintaining and reversing the expansion of said expandable portion.

6. The device of claim 5 wherein said means for maintaining and reversing said expansion is a clamp acting on said hollow member to selectively open and close a passage of said hollow member.

7. The device of claim 1 wherein said hollow member is comprised of a compressible biocompatible material, said compressible biocompatible material allowing the hollow member to conform to the natural shape of the urethra, thereby preventing deformation thereof.

8. A method of determining the length of a urethra comprising the following steps:

providing a device including a hollow member having an expandable portion at a first end, wherein said hollow member further includes a plurality of beads spaced equally apart from one another in a pre-defined pattern, each of the plurality of beads being located a prespecified distance from the first end of the hollow member, and being representative of a length of the urethra;

inserting said hollow member into the urethra until said hollow member is positioned in the bladder, expanding said expandable portion in the bladder and retracting said expandable portion until said hollow member anchors in the bladder neck;

maintaining said expansion of said expandable portion;

observing the one of said plurality of beads proximate the meatus when said hollow member is inserted into the urethra and said expandable portion is anchored in the bladder neck; and determining the length of the urethra based on the observed one of said plurality of beads.

9. The method of determining the length of a urethra according to claim 8, further comprising the steps of reversing said expansion of said expandable portion, and removing said device from the urethra.

10. The method of determining the length of a urethra according to claim 8 wherein said device further includes an external fluid source.

11. The method of determining the length of a urethra according to claim 10, further comprising interconnecting said external fluid source to said hollow member, and transmitting fluid from said external fluid source to said expandable portion.

12. The method of determining the length of a urethra according to claim 11 wherein said device further includes a means for controlling the transmission of fluid into and out of said expandable portion.

13. The method of determining the length of a urethra according to claim 12, wherein said steps of maintaining and reversing said expansion includes actuating said controlling means to selectively maintain and reverse the expansion of said expandable portion.

* * * * *